US 6,476,269 B2
Nov. 5, 2002

(54) METHOD FOR PRODUCING XYLYLENEDIAMINE

(75) Inventors: Kenichi Nakamura, Niigata (JP); Susumu Ōtsuka, Niigata (JP); Fumisada Kosuge, Niigata (JP); Takuji Shitara, Niigata (JP); Kazuhiko Amakawa, Niigata (JP)

(73) Assignee: Mitsubishi Gas Chemical Co. Inc., Tokyo (JP)

( * ) Notice: Subject to any disclaimer, the term of this patent is extended or adjusted under 35 U.S.C. 154(b) by 0 days.

(21) Appl. No.: 09/953,557

(22) Filed: Sep. 17, 2001

(65) Prior Publication Data

US 2002/0038054 A1 Mar. 28, 2002

(30) Foreign Application Priority Data

Sep. 25, 2000 (JP) ........................................ 2000-290459

(51) Int. Cl.7 .............................................. C07C 211/00
(52) U.S. Cl. ..................... 564/388; 564/395; 564/415
(58) Field of Search ................................. 564/388, 415, 564/395

(56) References Cited

PUBLICATIONS

Chem Abstract 1987:536278, Pryanikov et al, 1986.*

* cited by examiner

*Primary Examiner*—Samuel Barts
(74) *Attorney, Agent, or Firm*—Antonelli, Terry, Stout & Kraus, LLP

(57) ABSTRACT

A method for producing xylylenediamine by hydrogenating phthalonitrile synthesized through ammoxidation of xylene, wherein phthalonitrile is trapped in an organic solvent (A) by bringing a gas produced through ammoxidation into direct contact with the organic solvent (A), and hydrogenation including adding liquid ammonia to the resultant mixture is carried out without separation of phthalonitrile trapped in the organic solvent (A). Through this method, the phthalonitrile can be readily recovered from the produced gas and at high yield without need for new equipment, and xylylenediamine can be efficiently produced through hydrogenation. Xylylenediamine of high purity can be obtained by subjecting the produced xylylenediamine to extraction by use of an organic solvent (B) and water.

9 Claims, 1 Drawing Sheet

METHOD FOR PRODUCING XYLYLENEDIAMINE

BACKGROUND OF THE INVENTION

1. Field of the Invention

The present invention relates to a method for producing xylylenediamine by hydrogenating phthalonitrile obtained through ammoxidation of xylene.

Xylylenediamine is useful as a raw material of, for example, polyamide resins or epoxy curing agents, and as an intermediate material for producing isocyanates.

2. Background

In a well-known method for producing phthalonitrile, xylene is reacted through ammoxidation with ammonia and molecular oxygen in the presence of a catalyst. For example, Japanese Patent Application Laid-Open (kokai) No. Heisei 11(1999)-209332 discloses a method for producing phthalonitrile through ammoxidation by use of a catalyst containing a V-Cr-B-Mo oxide. The thus-produced phthalonitrile is hydrogenated in the presence of ammonia, to thereby produce xylylenediamine.

A gas produced during production of phthalonitrile through ammoxidation of xylene contains phthalonitrile (i.e., a target product), ammonia, carbon dioxide gas, carbon monoxide, hydrogen cyanide, aromatic amide, aromatic carboxylic acid, air, and steam. Therefore, before the phthalonitrile is subjected to hydrogenation, it must be separated from the produced gas through trapping.

In a proposed method for trapping and separating phthalonitrile from a gas produced through ammoxidation, the produced gas is introduced into a cooling apparatus having a large surface area; phthalonitrile is deposited and solidified on a cooling surface; and then phthalonitrile is collected after being melted. However, phthalonitrile is prone to undergo undesirable change (e.g., polymerization) at high temperature, and deteriorates when melted and removed, resulting in lowering of the purity of a product.

In a proposed method similar to the aforementioned method, the produced gas is introduced into a cooling apparatus; phthalonitrile is deposited and solidified on a cooling surface; a solvent is added to the solidified phthalonitrile; and the resultant mixture is fed to a hydrogenation reactor (*Kagaku Kogaku*, Vol. 32, No. 7, pp. 658–660 (1968)). However, in this method, phthalonitrile is prone to undergo change (e.g., polymerization) on the cooling surface of the cooling apparatus, to thereby generate a polymer which is insoluble in the added solvent, leading to maloperation of the apparatus due to accumulation of the polymer.

In another proposed trapping method, a gas produced through ammoxidation and containing phthalonitrile is brought into direct contact with water, phthalonitrile crystals are trapped while being suspended in the water, and phthalonitrile is separated from the suspension through solid-liquid separation (Process Handbook, edited by The Japan Petroleum Institute (1978)). Through this method, phthalonitrile is satisfactorily trapped. However, since the bulk specific gravity of phthalonitrile in the suspension is low, the slurry has a large volume. Therefore, separating solid and liquid from the aqueous slurry solution through filtration requires a very large filtration apparatus. In addition, the water content of crystals separated from the slurry solution is high, and thus a large amount of heat is necessary for drying the crystals.

Since phthalonitrile is relatively easily reacted with water at high temperature, to thereby form an amide of high boiling point, long-term heating of phthalonitrile in the presence of water causes lowering of the purity of phthalonitrile. When water is used as a trapping solvent, hydrogen cyanide, which is a by-product, is brought into contact with water at high temperature. Through the thermal process, hydrogen cyanide is easily transformed into, for example, formamide, ammonium formate, or a polymer. When such a substance is contained in wastewater, the substance causes an increase in TOD load and coloring of wastewater.

In still another proposed method for trapping and separating phthalonitrile from a gas produced through ammoxidation, the gas is brought into contact with an organic solvent (Process Handbook, edited by The Japan Petroleum Institute (1976)). In this method, after a solution in which phthalonitrile is trapped is subjected to distillation to thereby recover a solvent, rectification is carried out so as to purify phthalonitrile. Therefore, a large amount of energy is required for purification, and a large amount of phthalonitrile is lost.

In the subsequent step, phthalonitrile produced through ammoxidation is dissolved in ammonia or an organic solvent, and the resultant solution is subjected to hydrogenation.

When phthalonitrile is obtained in the form of solid or melt, a dissolution bath or a mixing bath is required for dissolving the phthalonitrile uniformly in a solvent prior to hydrogenation.

As described above, the conventional techniques—in which phthalonitrile is separated, through trapping, from a gas produced through ammoxidation, and the phthalonitrile is subjected to hydrogenation—have drawbacks; for example, the purity of phthalonitrile is lowered due to generation of by-products during separation of phthalonitrile from a gas produced through ammoxidation, waste or wastewater increases, and a large amount of energy is required.

In recent years, demand has arisen for polyamide resins or similar materials which are not easily colored, and therefore, xylylenediamine of higher purity is desired.

SUMMARY OF THE INVENTION

Thus, an object of the present invention is to provide a method for producing xylylenediamine by hydrogenating phthalonitrile synthesized through ammoxidation of xylene, comprising recovering phthalonitrile, readily and at high yield, from a gas produced through ammoxidation, to thereby efficiently produce xylylenediamine of high purity.

In view of the foregoing, the present inventors have performed extensive studies, and have found that, by bringing a gas produced through ammoxidation into direct contact with an organic solvent (A), phthalonitrile can be trapped in the organic solvent (A), and through hydrogenation including adding liquid ammonia to the resultant mixture without separation of phthalonitrile trapped in the organic solvent (A), the phthalonitrile can be readily recovered from the produced gas and at high yield without need for new equipment, and xylylenediamine can be efficiently produced through hydrogenation; and that, by subjecting the produced xylylenediamine to extraction by use of an organic solvent (B) and water, xylylenediamine of high purity can be obtained. The present invention has been accomplished on the basis of these findings.

Accordingly, the present invention provides a method for producing xylylenediamine by hydrogenating phthalonitrile synthesized through ammoxidation of xylene, which method comprises:

(1) an ammoxidation step for producing phthalonitrile by causing xylene to react in a vapor-solid catalytic manner with ammonia and an oxygen-containing gas, to thereby cause ammoxidation;

(2) a trapping step for trapping phthalonitrile in an organic solvent (A) by bringing a gas produced through ammoxidation into direct contact with the organic solvent (A); and (3) a hydrogenation step for carrying out hydrogenation including adding liquid ammonia to phthalonitrile without separating the phthalonitrile trapped in the organic solvent (A).

There is also provided a method for producing xylylenediamine according to the aforementioned method, which method further comprises:

(4) a separation step for separating ammonia and the organic solvent (A) or ammonia from a hydrogenation product, to thereby obtain crude xylylenediamine;

(5) an extraction step for adding to the crude xylylenediamine water, or water and an organic solvent (B), to thereby separate the resultant mixture into an organic solvent phase and an aqueous phase; and (6) a recovery step for recovering xylylenediamine of high purity from the aqueous phase which has been separated through extraction.

BRIEF DESCRIPTION OF THE DRAWING

In FIG. 1, reference character A represents an ammoxidation step, B a trapping step, C a hydrogenation step, D a separation step, E an extraction step, and F a recovery step.

DETAILED DESCRIPTION OF PREFERRED EMBODIMENTS

Figure 1:
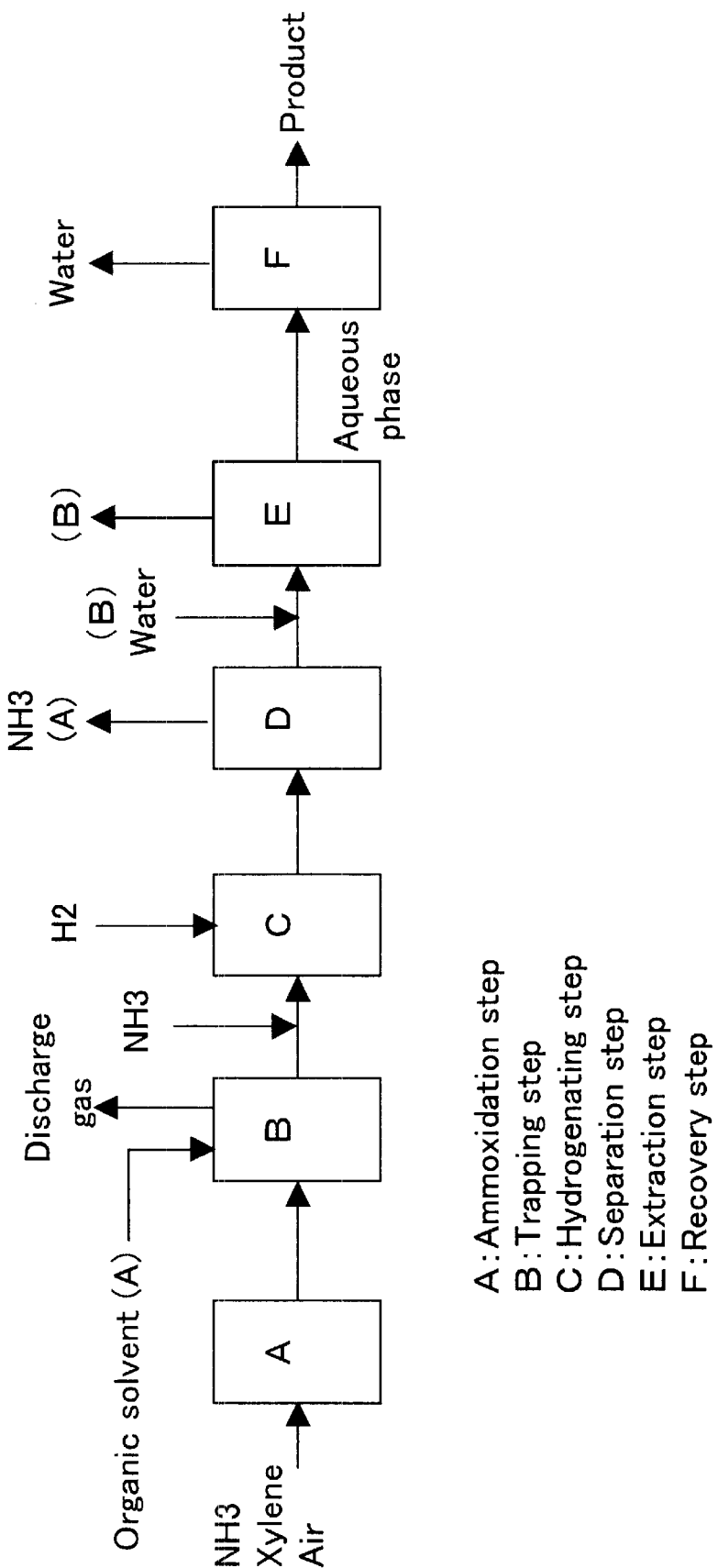
FIG. 1 is a flow chart showing an embodiment of the method for producing xylylenediamine of the present invention.

In the present invention, xylene is used as a raw material. Particularly, m-xylene and p-xylene are preferably used. Isophthalonitrile and terephthalonitrile are produced through ammoxidation of m-xylene and p-xylene, respectively, and, through the subsequent hydrogenation, isophthalonitrile and terephthalonitrile are converted into m-xylylenediamine and p-xylylenediamine, respectively.

<Ammoxidation Step>

Since ammoxidation generates a large amount of heat of reaction, the reaction is preferably carried out in a vapor-phase fluidized manner so as to attain a uniform temperature profile in the reactor. A catalyst containing an oxide of at least one metal selected from among vanadium, molybdenum, and iron is preferably used. In order to enhance the activity, strength, and lifetime of the catalyst, the metal oxide is modified through addition of another metal oxide containing at least one element selected from the group consisting of Mg, Ca, Ba, La, Ti, Zr, Cr, W, Co, Ni, B, Al, Ge, Sn, Pb, P, Sb, Bi, Li, Na, K, Rb, and Cs. The resultant catalyst containing an oxide of a plurality of metals is represented by the following formula.

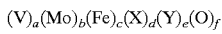

$(V)_a(Mo)_b(Fe)_c(X)_d(Y)_e(O)_f$

In the above formula, X represents at least one element selected from the group consisting of Mg, Ca, Ba, La, Ti, Zr, Cr, W, Co, and Ni; Y represents at least one element selected from the group consisting of B, Al, Ge, Sn, Pb, P, Sb, Li, Na, K, Rb, and Cs; a, b, c, d, and e represent atomic proportions; a=0.01–1 (preferably 0.1–0.7); b=0.01–1 (preferably 0.05–0.7); c=0–1; d=0–1 (preferably 0.05–0.7); e=0–1 (preferably 0.05–0.7); and f represents the number of oxygen atoms contained in the above formula of the oxide composed of the aforementioned elements.

The oxygen-containing gas to be used in ammoxidation is usually air, and oxygen-enriched air may also be used. A diluent such as nitrogen or carbon dioxide gas may be used in combination. Oxygen is used in an amount by mol of at least 1.5 times, preferably 2–50 times, the amount by equivalent (in terms of methyl group) of xylene. When the amount of oxygen is less than the lower limit, the yield of a nitrile compound decreases, whereas when the amount of oxygen exceeds the upper limit, space-time yield decreases.

When ammoxidation is performed by use of air, the concentration of xylene contained in a raw material gas to be fed to the reactor is 0.2–10 vol. %, preferably 0.5–5 vol. %. When the concentration exceeds the upper limit, the yield of a nitrile compound decreases, whereas when the concentration is less than the lower limit, space-time yield decreases.

Ammonia of industrial grade can be used for ammoxidation. Ammonia is used in an amount by mol of 1–10 times, preferably 3–7 times, the amount by equivalent (in terms of methyl group) of xylene. When the amount of ammonia is less than the lower limit, the yield of a nitrile compound decreases, whereas when the amount exceeds the upper limit, space-time yield decreases.

Ammoxidation is carried out preferably in a fluidized-bed reactor, and a variety of fluidized-bed reactors can be used. Ammonia may be supplied to the reactor in the form of a mixture with xylene, or ammonia and xylene may be supplied to the reactor separately. In an alternative scheme, ammonia and xylene are mixed with a portion of an oxygen-containing gas, and the resultant mixture is supplied to the reactor.

The temperature of ammoxidation is 300–500° C., preferably 330–470° C. When the reaction temperature is lower than the lower limit, percent conversion decreases, whereas when the reaction temperature exceeds the upper limit, the amount of by-products such as carbon dioxide gas and hydrogen cyanide increases, to thereby decrease the yield of a nitrile compound. Ammoxidation may be carried out under ambient pressure, reduced pressure, or pressurized conditions, and a pressure of approximately ambient pressure to 0.2 MPa is preferred. Although the time of contact between the reaction gas and a catalyst varies in accordance with conditions such as the type of raw material, the mol ratio of the fed ammonia or oxygen-containing gas to the fed m-xylnene, and the reaction temperature, the contact time is usually 0.3–30 seconds.

A gas produced in the ammoxidation reactor contains unreacted xylene, nitrile compounds such as phthalonitrile, ammonia, hydrogen cyanide, carbon dioxide gas, steam, carbon monoxide, nitrogen, oxygen, and other substances.

<Trapping Step>

In the subsequent trapping step, the produced gas is brought in to contact with an organic solvent (A) in a phthalonitrile trapping apparatus, to thereby dissolve phthalonitrile in the solvent, thereby separating the phthalonitrile from the pro duced gas. P referably, the organic solvent (A) has a boiling point higher than that of xylene serving as a raw material, has high solubility to phthalonitrile, is inert to phthalonitrile, and does not have a functional group which is to be hydrogenated. When the boiling poin t of the organic solvent (A) is low, the amount of the solvent entrained by the remaining gas increases.

Specific examples of the organic solvent (A) include C6–C12 aromatic hydrocarbons such as toluene, m-xylene, p-xylene, mesitylene, pseudocumene, and tetramethylbenzene. Of these, mesitylene, pseudocumene, and a mixture thereof are preferably used.

The phthalonitrile trapping apparatus is operated under the conditions such that the temperature of a liquid phase portion is equal to or lower than the boiling point of the solution contained in the apparatus. The apparatus may be operated under ambient pressure, reduced pressure, or pressurized conditions, but is usually operated at ambient pressure to the pressure of ammoxidation.

Aamonia, hydrogen cyanide, carbon dioxide gas, water, carbon monoxide, nitrogen, oxygen, etc. contained in the gas produced through ammoxidation are not absorbed in the organic solvent, and are discharged from the phthalonitrile trapping apparatus in the form of gas.

Liquid ammonia is added to phthalonitrile absorbed in the organic solvent (A) without separating the organic solvent (A), and the resultant mixture is subjected to subsequent hydrogenation.

<Hydrogenation Step>

In the hydrogenation step, production of xylylenediamine through hydrogenation of phthalonitrile is preferably carried out by use of a catalyst predominantly containing nickel and/or cobalt. Hydrogenation of phthalonitrile in the presence of ammonia may be carried out by use of a platinum-group catalyst. However, when a platinum-group catalyst such as a ruthenium catalyst is used, nucleus hydrogenation of produced xylylenediamine and an aromatic hydrocarbon (e.g., mesitylene or pseudocumene) serving as the organic solvent (A) proceeds, which is undesirable. Therefore, as in the case of the present invention, when the solvent for trapping phthalonitrile and contained in the gas produced through ammoxidation is the same as the solvent used for hydrogenation, a catalyst predominantly containing nickel or cobalt is preferably used.

The composition of the raw material to be fed to a hydrogenation reactor is appropriately determined arbitrarily. When the concentration of phthalonitrile serving as a reactant is lower and when the concentration of ammonia serving as a solvent is higher, the yield of xylylenediamine becomes higher. In order to attain satisfactory yield and productivity, the composition of the raw material is regulated through further addition of the organic solvent (A) or ammonia. The composition of the raw material is preferably determined so as to attain the following compositional proportions: phthalonitrile (1–10 wt. %), the organic solvent (A) (1–50 wt. %), and ammonia (20–97 wt. %).

Hydrogenation may be carried out in a batch-type process or a continuous process. In a batch-type process, hydrogenation may be carried out in a tank reactor in which the raw material is completely mixed with a powdery catalyst of a Raney metal such as nickel or cobalt. Industrially, hydrogenation is carried out in a simple manner through a method employing an trickle-type continuous reactor including a tubular reactor and a molded catalyst provided on a fixed bed, in which the raw material solution and hydrogen gas are fed in parallel through the upper section of the reactor.

A catalyst comprising nickel and/or cobalt supported on a carrier is preferably used as a hydrogenation catalyst. Examples of the carrier employed include diatomaceous earth, silicon oxide, alumina, silica-alumina, titanium oxide, zirconium oxide, and carbon.

When a nickel catalyst is used as a hydrogenation catalyst, the reaction temperature is 60–130° C., and the reaction pressure is 4–15 MPa.

<Separation Step>
<Separation Step>

A reaction mixture containing xylylenediamine is obtained through the aforementioned hydrogenation. Crude xylylenediamine can be obtained by separating ammonia, or by separating ammonia and the organic solvent (A), from the reaction mixture.

If the organic solvent (A) can be separated from the aqueous phase by adding water to the reaction mixture, a solvent of the same species as the organic solvent (A) may be employed as organic solvent (B). When the organic solvent (A) is of the same species as the organic solvent (B), separation of the organic solvent (A) is unnecessary.

Separation of ammonia or ammonia and organic solvent (A) from the reaction mixture is preferably carried out through distillation. If necessary, a plurality of distillation columns may be used. The separated ammonia can be circulated and recycled in the ammoxidation step or the hydrogenation step. The separated solvent can be circulated and recycled in the trapping step. When ammonia or organic solvent (A) is recycled, an additional purification step may be provided for purifying ammonia or organic solvent (A).

<Extraction Step>

Crude xylylenediamine contains impurities which cannot be separated therefrom through distillation. Water, or water and organic solvent (B) are added to the crude xylylenediamine, and the impurities are trapped in the organic solvent through extraction. Xylylenediamine is recovered in the aqueous phase.

When only ammonia is separated in the separation step and a mixture of crude xylylenediamine and organic solvent (A) is supplied in the extraction step, organic solvent (B) which is of the same species as the organic solvent (A) may further be added as an additional organic solvent (A) in order to enhance extraction efficiency. Alternatively, organic solvent (B) which is of a species different from organic solvent (A) may be added. When organic solvent (B) is of the same species as organic solvent (A), operation for separating the organic solvent is simplified in a xylylenediamine production apparatus.

No particular limitation is placed on the organic solvent (B), so long as the solvent can be separated from the aqueous phase. Preferred examples of the organic solvent (B) include C5–C12 aromatic hydrocarbons, C5–C12 saturated aliphatic hydrocarbons, and C5–C12 saturated alicyclic hydrocarbons. Specific examples include benzene, toluene, mxylene, p-xylene, mesitylene, pseudocumene, hexane, and cyclohexane. These organic solvents (B) may be used singly or in combination of two or more species. Of these, xylene serving as a raw material (e.g., m-xylene in the case of production of m-xylylenediamine) is advantageously used, since the number of compounds employed is reduced.

The amount of the organic solvent (B) employed is 0.01–100 parts by weight on the basis of 1 part by weight of the crude xylylenediamine. In consideration of extraction efficiency, the amount of the organic solvent (B) is preferably 0.2–10 parts by weight on the basis of 1 part by weight of crude xylylenediamine.

Similar to the case of the organic solvent (B), the amount of water employed is 0.01–100 parts by weight, preferably 0.2–10 parts by weight, on the basis of 1 part by weight of crude xylylenediamine.

The extraction temperature is not particularly limited, and extraction is carried out satisfactorily at room temperature.

Extraction operation may be carried out repeatedly. After the organic solvent phase containing impurities has been separated from the aqueous phase, organic solvent (B) is added to the aqueous phase, and impurities are trapped in the solvent through extraction. By repeating such an operation, the purity of xylylenediamine can be enhanced.

<Recovery Step>

When the xylylenediamine-containing aqueous phase obtained in the extraction step is subjected to purification, xylylenediamine of high purity can be produced. Purification can be carried out preferably through customary batch distillation or continuous distillation.

The organic solvent (B) recovered from the organic solvent phase can be recycled in the extraction step. When organic solvent (A) is not separated in the separation step, the organic solvent (A) is recovered in the recovery step, and the recovered solvent can be recycled in the trapping step.

The present invention will next be described in detail with reference to the drawing. FIG. 1 is a flow chart showing an embodiment of the method for producing xylylenediamine of the present invention.

As shown in FIG. 1, in ammoxidation step A, air, ammonia, and xylene are fed to an ammoxidation reactor filled with a catalyst. A gas produced through ammoxidation contains unreacted xylene, nitrile compounds such as phthalonitrile, ammonia, hydrogen cyanide, carbon dioxide gas, steam, carbon monoxide, nitrogen, and oxygen.

The produced gas is forwarded to trapping step B, and is brought into contact with organic solvent (A). Phthalonitrile is dissolved in the organic solvent (A), and separated from the produced gas. Ammonia, hydrogen cyanide, A carbon dioxide gas, steam, carbon monoxide, nitrogen, oxygen, etc. which have not been absorbed in the solvent are discharged from the top of a trapping apparatus. The phthalonitrile absorbed in the organic solvent (A) is removed from the bottom of the trapping apparatus. Liquid ammonia is added to the removed phthalonitrile, and the resultant liquid is forwarded to hydrogenation step C.

In hydrogenation step C, the aforementioned phthalonitrile-dissolved liquid and hydrogen are fed to a hydrogenation reactor filled with a catalyst, and a reaction mixture containing xylylenediamine is discharged from the reactor.

The reaction mixture is forwarded to separation step D. In separation step D, organic solvent (A), ammonia, etc. are separated from the reaction mixture, to thereby yield crude xylylenediamine.

An organic solvent (B) and water are added to the crude xylylenediamine, and the resultant mixture is forwarded to extraction step E. In extraction step E, impurities are trapped in the organic solvent phase through extraction, and xylylenediamine is recovered in the aqueous phase.

In recovery step F, xylylene diamine of high purity is recovered from the aqueous phase through distillation.

As described below in the Examples, according to the present invention, high amine yield is attained, since phthalonitrile is subjected to hydrogenation including direct addition of ammonia to the phthalonitrile which has been separated from a gas produced through ammoxidation and trapped in an organic solvent (A).

According to the present invention, a process for producing xylylenediamine is greatly simplified, since phthalonitrile separated from a gas produced through ammoxidation is trapped in organic solvent (A), and ammonia is added to the phthalonitrile-trapped solvent, without subjecting to further treatment, so as to cause hydrogenation. In addition, generation of impurities in the produced phthalonitrile, a decrease in yield of phthalonitrile, and generation of waste are not observed. Thus, xylylenediamine can be produced economically advantageously through a simple, clean process.

In the present invention, xylylenediamine of high purity is produced from crude xylylenediamine through extraction and distillation. Thus, a polymer of high quality can be synthesized from xylylenediamine produced through the method of the present invention.

EXAMPLES

The present invention will next be described in more detail by way of Examples, which should not be construed as limiting the invention thereto.

In the below-described Examples, analysis of the compositions of reaction products, extracts, or products was carried out by means of gas chromatography.

<Preparation of Ammoxidation Catalyst>

Vanadium pentoxide ($V_2O_5$) (229 g) was added to water (500 mL), to thereby yield a mixture, and an aliquot of oxalic acid (477 g) was added to the mixture with stirring at 80–90° C. so as to dissolve the vanadium compound, to thereby yield a solution of vanadium oxalate. Another aliquot of oxalic acid (963 g) was added to water (400 mL), and the resultant mixture was heated to 50–60° C. To the mixture, a solution of chromic anhydride ($CrO_3$) (252 g) in water (200 mL) was added under sufficient stirring so as to dissolve the components, to thereby yield a solution of chromium oxalate. The thus-yielded solutions were mixed at 50–60° C., to thereby prepare a V-Cr-containing solution. To the V-Cr-containing solution were added a solution of phosphomolybdic acid ($H_3(PMo_{12}O_{40}).20H_2O$) (41.1 g) dissolved in water (100 mL), and a solution of potassium acetate ($CH_3COOK$) (4.0 g) dissolved in water (100 mL). Subsequently, a 20 wt. % aqueous silica sol (containing $Na_2O$ (0.02 wt. %)) (2,500 g) was added, to thereby form a slurry.

Boric acid ($H_3BO_3$) (78 g) was added to the slurry, and the resultant mixture was concentrated by heating until the liquid amount became approximately 3,800 g. The thus-concentrated mixture containing catalyst components was dried by use of a spray drier while the inlet temperature and the outlet temperature were maintained at 250° C. and 130° C., respectively. The dried mixture was further dried by means of a drier at 130° C. for 12 hours, and the resultant mixture was fired at 400° C. for 0.5 hours and at 550° C. for eight hours under air flow, to thereby obtain a catalyst to be used in a fluidized process. The obtained catalyst was found to have atomic proportions of V:Cr:B:Mo:P:Na:K= 1:1:0.5:0.086:0.007:0.009:0.020 and an effective catalyst component content of 50 wt. %.

Example 1

Ammoxidation Step to Hydrogenation Step

Ammoxidation, trapping of phthalonitrile, and hydrogenation were performed on the basis of the process flow shown in FIG. 1.

The catalyst (6 L) which had been prepared in the aforementioned manner was charged into ammoxidation reactor A. After air, m-xylene (MX), and ammonia had been mixed and pre-heated to 350° C., the resultant mixture was fed to the reactor. The following feed conditions were employed: an amount of fed MX of 350 g/Hr; a mol ratio of $NH_3/MX$ of 11; a mol ratio of $O_2/MX$ of 5.4; and an SV of 630 $Hr^{-1}$. The temperature and pressure for reaction were 420° C. and 0.2 MPa-G, respectively.

The produced gas supplied from the top of the reactor was forwarded to trapping apparatus B. Pseudocumene serving as organic solvent (A) was fed to the trapping apparatus, and the gas produced through ammoxidation was blown into a liquid phase contained in the trapping apparatus, which was maintained at 140° C. Isophthalonitrile was dissolved and absorbed in pseudocumene, and the resultant solution was removed from the bottom of the trapping apparatus. Gas components including carbon dioxide gas, ammonia, hydrogen cyanide, carbon monoxide, nitrogen, oxygen, and steam were removed from the top of the trapping apparatus.

Liquid ammonia was added to the isophthalonitrile-containing pseudocumene solution removed from the bottom of the trapping apparatus B, and the resultant solution was employed as a raw material for hydrogenation. The proportions of isophthalonitrile/pseudocumene/ammonia in the solution were 6/25/69 by weight.

An Ni/diatomaceous earth catalyst (Ni content: 50 wt. %) (5 kg) was charged into vertical tubular hydrogenation reactor C (volume: 4 L). Through the upper section of the reactor, a raw material containing isophthalonitrile, pseudocumene, and ammonia was fed at a rate of 6 kg/hr. Hydrogen was fed through the upper section of the reactor in parallel with the raw material, and hydrogenation was carried out at a reaction pressure of 12 MPa and at 90° C.

Through hydrogenation, the yield of m-xylylenediamine was 92% on the basis of isophthalonitrile.

Example 2

The procedure of Example 1 was repeated, except that mesitylene was used as organic solvent (A) for trapping isophthalonitrile, 50 wt. %-Co/diatomaceous earth was used as a hydrogenation catalyst, and the reaction temperature was changed to 120° C. Through hydrogenation, the yield of m-xylylenediamine was 94% on the basis of isophthalonitrile.

Example 3

The procedure of Example 1 was repeated, except that p-xylene was used as a raw material for ammoxidation, pseudocumene was used as organic solvent (A) for trapping the resultant terephthalonitrile, and 50 wt. %-Ni/diatomaceous earth was used as a hydrogenation catalyst. Through hydrogenation, the yield of p-xylylenediamine was 92% on the basis of terephthalonitrile.

Example 4

Separation Step to Recovery Step

Trapping solvent (A) (i.e., pseudocumene) and ammonia were separated, through distillation, from the hydrogenation reaction mixture obtained in Example 1, and the resultant mixture was further subjected to distillation, to thereby remove low-boiling-point by-products and high-boiling-point by-products, yielding crude m-xylylenediamine.

The thus-yielded crude m-xylylenediamine was found to contain, as impurities, methylbenzylamine (200 ppm), dimethylbenzyl alcohol derived from the solvent (A) (1,500 ppm), and unknown high- and low-boiling-point components (300 ppm).

To the crude m-xylylenediamine, m-xylene serving as extraction solvent (B) (1 kg) and water (1 kg) were added at room temperature, and the resultant mixture was stirred. After the mixture was allowed to stand, an m-xylene phase was separated from the mixture through extraction.

This extraction operation was carried out four times, and an aqueous phase containing m-xylylenediamine was obtained.

The m-xylylenediamine-containing aqueous phase was subjected to batch distillation, to thereby remove water, and subsequently a portion of an initial distillate was removed, to thereby yield m-xylylenediamine of high purity. The m-xylylenediamine had a purity of 99.99 wt. %, and was found to contain methylbenzylamine (31 ppm), unknown high- and low-boiling-point components (10 ppm or less), and no dimethylbenzyl alcohol.

Example 5

Separation Step to Recovery Step

Only ammonia was separated, through distillation, from the hydrogenation reaction mixture obtained in Example 1. Water (1 kg) was added to the resultant mixture (5 kg) containing crude m-xylylenediamine and solvent (A) (i.e., pseudocumene) at room temperature, with stirring. After the mixture was allowed to stand, a pseudocumene phase was separated from the mixture through extraction.

Pseudocumene (1 kg) was further added to the resultant aqueous phase containing m-xylylenediamine, and stirred. After the mixture was allowed to stand, a pseudocumene phase was separated from the mixture through extraction.

The m-xylylenediamine-containing aqueous phase obtained through four times repetitions of extraction operations was subjected to batch distillation, to thereby remove water, and subsequently a portion of an initial distillate was removed, to thereby yield m-xylylenediamine of high purity. The m-xylylenediamine had a purity of 99.99 wt. %, and was found to contain methylbenzylamine (48 ppm), unknown high- and low-boiling-point components (10 ppm or less), and no dimethylbenzyl alcohol.

What is claimed is:

1. A method for producing xylylenediamine by hydrogenating phthalonitrile synthesized through ammoxidation of xylene, which method comprises:

p1(1) an ammoxidation step for producing phthalonitrile by causing xylene to react in a vapor-solid catalytic manner with ammonia and an oxygen-containing gas, to thereby cause ammoxidation;

p1(2) a trapping step for trapping phthalonitrile in an organic solvent (A) by bringing a gas produced through ammoxidation into direct contact with the organic solvent (A); and p1(3) a hydrogenation step for carrying out hydrogenation including adding liquid ammonia to phthalonitrile without separating the phthalonitrile trapped in the organic solvent (A).

2. A method for producing xylylenediamine according to claim 1, wherein ammoxidation of xylene is carried out in the presence of a fluidized catalyst containing a metal oxide, the metal being at least one element selected from vanadium, molybdenum, and iron.

3. A method for producing xylylenediamine according to claim 1, wherein the organic solvent (A) used in the trapping step is a C6–C12 aromatic hydrocarbon.

4. A method for producing xylylenediamine according to claim 3, wherein the organic solvent (A) used in the trapping step is mesitylene and/or pseudocumene.

5. A method for producing xylylenediamine according to claim 1, wherein a nickel catalyst and/or a cobalt catalyst is employed in the hydrogenation step.

6. A method for producing xylylenediamine according to claim 1, further comprising:

p1(4) a separation step for separating ammonia and the organic solvent (A) or ammonia from a hydrogenation product, to thereby obtain crude xylylenediamine;

p1(5) an extraction step for adding to the crude xylylenediamine water, or water and an organic solvent (B), to thereby separate the resultant mixture into an organic solvent phase and an aqueous phase; and p1(6) a recovery step for recovering xylylenediamine of high purity from the aqueous phase which has been separated through extraction.

7. A method for producing xylylenediamine according to claim 6, wherein the organic solvent (B) used in the extraction step is at least one compound selected from among C5–C12 aromatic hydrocarbons, saturated aliphatic hydrocarbons, and saturated alicyclic hydrocarbons.

8. A method for producing xylylenediamine according to claim 6, wherein the organic solvent (B) used in the extraction step is xylene of a species same as that used as a raw material.

9. A method for producing xylylenediamine according to claim 6, wherein only ammonia is separated in the separation step, and the organic solvent (B) used in the extraction step is a species similar to the organic solvent (A) used in the trapping step.

* * * * *